United States Patent [19]

Inoue

[11] Patent Number: 5,423,631
[45] Date of Patent: Jun. 13, 1995

[54] ANTIFOULING STRUCTURES

[75] Inventor: Shunji Inoue, Nagoya, Japan

[73] Assignee: NGK Insulators, Ltd., Japan

[21] Appl. No.: 27,779

[22] Filed: Mar. 8, 1993

[30] Foreign Application Priority Data

| Mar. 24, 1992 | [JP] | Japan | 4-066266 |
| Mar. 24, 1992 | [JP] | Japan | 4-066267 |
| Mar. 24, 1992 | [JP] | Japan | 4-066268 |
| Apr. 2, 1992 | [JP] | Japan | 4-081049 |

[51] Int. Cl.$^6$ .............. E02D 31/00; C23F 13/00
[52] U.S. Cl. .................. 405/211; 204/148; 204/197; 405/127; 405/216
[58] Field of Search ......... 405/211, 195.1, 303; 204/196, 197, 147, 148

[56] References Cited

U.S. PATENT DOCUMENTS

| 2,139,497 | 12/1938 | Hansel et al. | |
| 2,422,477 | 6/1947 | Driver | |
| 3,103,103 | 9/1963 | Liddell | |
| 3,137,642 | 6/1964 | Johns | 204/148 |
| 3,260,661 | 7/1966 | Kemp et al. | 204/148 |
| 3,455,808 | 7/1969 | Raclot | 204/148 |
| 3,620,943 | 11/1971 | White | 204/148 |
| 3,819,439 | 4/1974 | Taylor | 156/89 |
| 4,202,858 | 5/1980 | Bruce et al. | |
| 4,219,889 | 8/1980 | Parssinen et al. | 367/158 |
| 4,267,210 | 5/1981 | Yajima et al. | 427/226 |
| 4,317,559 | 3/1982 | Finkbeiner et al. | 251/331 |
| 4,496,444 | 1/1985 | Bagnulo | 204/147 |
| 4,551,187 | 11/1985 | Church et al. | |
| 4,678,692 | 7/1987 | Porter | |
| 5,248,351 | 9/1993 | Kubozono et al. | 148/414 |

FOREIGN PATENT DOCUMENTS

| 0510850 | 10/1992 | European Pat. Off. |
| 2268847 | 11/1975 | France |
| 2040232 | 8/1980 | United Kingdom |
| 2179271 | 3/1987 | United Kingdom |
| WO82/02525 | 8/1982 | WIPO |

Primary Examiner—Dennis L. Taylor
Attorney, Agent, or Firm—Parkhurst, Wendel & Rossi

[57] ABSTRACT

The invention provides an antifouling structure that excels in antifouling performance and durability, dispenses with maintenance work, poses no toxicity problem, and is easily handled. The antifouling structure is in a flexible thin sheet, and comprises a copper alloy and an insulating material layer. The copper alloy has a Be content of 0.2 to 2.8% by weight. The insulating layer material, for instance, is made of at least one of methyl methacrylate-modified natural rubber, nitrile rubber and chlorinated rubber. This rubber is dissolved in a suitable solvent for primer or other treatment, coated on the required surface area of the copper alloy layer, and dried to obtain an insulating material layer having a given thickness. The antifouling structure is bonded to the inner wall of a water intake pipe to form a three-layer structure made up of iron, insulating material and beryllium-copper, thereby inhibiting deposition of marine organisms and enabling the function of inhibiting marine deposits to be maintained due to the continued liberation of copper or beryllium ions.

13 Claims, 6 Drawing Sheets

ANTIFOULING STRUCTURES

BACKGROUND OF THE INVENTION

The present invention relates to an antifouling structure and method effective to inhibit deposition of marine organisms such as barnacles, blue mussels and seaweed.

Offshore structures in contact with seawater are always exposed to contamination by marine organisms, resulting in damage to appearance or malfunction. For instance, ships suffer a driving force drop when many forms of oceanic organisms are deposited onto their bottoms, etc., and thermoelectric power plants are forced to stop operation when various forms of oceanic organisms are built up on their seawater intake pits, because a serious problem arises in connection with the circulation of a seawater serving as a cooling medium.

Among scores of techniques for inhibiting marine deposits studied so far in the art, there is typically now available a method for protecting an offshore structure against contamination, in which the surface of that structure in contact with seawater is coated with a coating material containing cuprous oxide or organotin.

A grave problem with this conventional method, however, is that the coating material has a service life as short as one year, since even when applied in a thick layer, it is likely to peel away. Accordingly, is needed troublesome maintenance work is necessary in which the coating material must be renewed per year.

Another method is disclosed in JP-A-60-209505 that is directed to a member for inhibiting marine deposits, which comprises copper or a copper (e.g., Cu-Ni) alloy. However, this method is found to be less than satisfactory in terms of corrosion resistance and antifouling effect.

Our years of study have now revealed that the application of a beryllium-copper alloy to an offshore structure achieves a much-more excellent antifouling effect. The reason would be that beryllium and copper ions interact synergistically, producing a great effect on inhibiting oceanic organisms from having access to the offshore structure and preventing their propagation. In other words, we have now found that the beryllium-copper alloy has a combined effect both on inhibiting marine deposits and on the continued liberation of copper ions.

A main object of the invention is to provide an antifouling structure that excels in antifouling properties and durability, dispenses with maintenance work, offers no toxicity problem, and is easy to handle.

Another object of the invention is to provide a method for fixing an antifouling structure to an application member, which enables the antifouling structure to be well fixed to the application member, excel in antifouling properties and durability, dispense with maintenance work, and present no toxicity problem.

A further object of the invention is to provide a structure for preventing deposition of organisms, which is well fixed to an application (or associated )member, excels in antifouling properties and durability, dispenses with maintenance work, and offers no toxicity problem.

SUMMARY OF THE INVENTION

According to one aspect of the invention, there is provided an antifouling structure characterized by being a flexible thin sheet made up of a copper alloy and an insulating material layer. Preferably, this antifouling structure comprises a copper alloy layer, an insulating material layer provided on the surface of the copper alloy layer, and an adhesive material layer provided on the insulating material layer. More preferably, the insulating material layer is bonded or otherwise fixed to a metal member.

According to another aspect of the invention, there is provided an antifouling structure characterized by being an inflexible sheet member made up of a thin sheet made of a copper alloy and an insulator layer. Preferably, an additional adhesive layer is provided on the surface of the insulator layer. More preferably, the member to which the adhesive layer is bonded is a metal. By way of example but not by way of limitation, the insulator layer may be formed of synthetic resin, tile material or hard rubber.

According to a further aspect of the invention, there is provided a method for installing an antifouling structure, characterized in that an insulator layer is formed on the surface of a metal member, and a thin sheet made up of a copper alloy is bonded to the surface of the insulator layer.

According to a still further aspect of the invention, there is provided a structure for inhibiting deposition of organisms, characterized by comprising a metal member, an insulator layer formed on the surface of the metal member, and a metal gauze made up of a copper alloy is bonded to the surface of the insulator layer.

BRIEF DESCRIPTION OF THE DRAWINGS

The invention will now be explained, more specifically but not exclusively, with reference to the accompanying drawings, in which.

DESCRIPTION OF THE PREFERRED EMBODIMENTS

Figure 1:
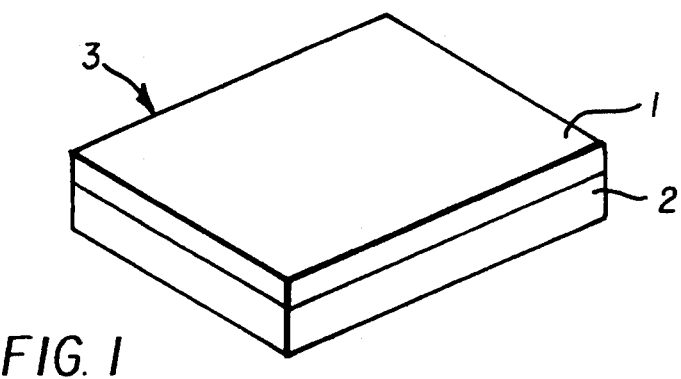
FIG. 1 is a schematic, perspective view of the first embodiment of the antifouling structure according to the first aspect of the invention.

It is preferable to use a beryllium-copper alloy for the copper alloy in the invention. This beryllium-copper alloy has a beryllium content ranging from 0.2% by weight to 2.8% by weight, and may be selected from the group consisting of Be-Cu, Be-Co-Cu, Be-Co-Si-Cu and Be-Ni-Cu alloys.

Typical compositions of the copper alloy used in the invention are:

(1) 0.2 to 1.0% by weight of beryllium, 2.4 to 2.7% by weight of cobalt and the balance being copper and inevitable impurities, (2) 0.2 to 1.0% by weight of beryllium, 1.4 to 2.2% by weight of nickel and the balance being copper and inevitable impurities, (3) 1.0 to 2.0% by weight of beryllium, 0.2 to 0.6% by weight of cobalt and the balance being copper and inevitable impurities, and (4) 1.6 to 2.8% by weight of beryllium, 0.4 to 1.0% by weight of cobalt, 0.2 to 0.35% by weight of silicon and the balance being copper and inevitable impurities.

Preferably, the contents of beryllium (Be), cobalt (Co), nickel (Ni) and silicon (Si) selectively incorporated in the copper alloy lie in the respective ranges:

Beryllium—0.2 to 2.8% by weight
Cobalt—0.2 to 2.7% by weight
Nickel—1.4 to 2.2% by weight
Silicon—0.2 to 0.35% by weight Set out below are for what purpose the above elements are added for and why the upper and lower limits thereof are set at the above values.

Beryllium: 0.2–2.8% by weight

Beryllium is used to (1) protect the structure, when immersed in seawater, against contamination by liberating beryllium ions, (2) improve the strength and properties, e.g., corrosion resistance, of the copper alloy, (3) enhance the productivity of the copper alloy as by heat treatment and grain size regulation, and (4) improve the processability and castability of the copper alloy. At below 0.2% by weight the above-described effects (1)–(4) are unachievable. At higher than 2.8% by weight, not only is there some metalleability drop but a cost-effective problem arises as well.

Cobalt: 0.2 to 2.7% by weight

Cobalt is used to form a fine CoBe compound and disperse it throughout the alloy matrix, thereby improving the mechanical properties and productivity of the copper alloy. At less than 0.2% by weight this effect is not well achievable. At higher than 2.7% by weight, not only is there some material flowability drop but there is little or no improvement in the above-described effect as well. In addition, a cost-effective problem arises.

Nickel: 1.4–2.2% by weight

Nickel is used to form a fine NiBe compound and disperse it throughout the alloy matrix, thereby improving the mechanical properties and productivity of the copper alloy. At less than 1.4% by weight this effect is not well achievable. At higher than 2.2% by weight, not only is there some material flowability drop but there is little or no improvement in the above-described effect as well. In addition, a cost-effective problem arises.

Silicon: 0.2–0.35% by weight

Silicon is used to improve the material flowability of the copper alloy. At less than 0.2% by weight this effect is not well achievable. At higher than 0.35% by weight the resulting alloy becomes brittle with a toughness drop.

As a result of our years of experimentation and research, it has turned out that the beryllium-copper alloy has a combined effect both on preventing contamination and on the continued liberation of copper ions. Detailed explanation will now be made to the antifouling effect and the continued action on liberating copper ions.

(1) Antifouling Effect

Figure 4:
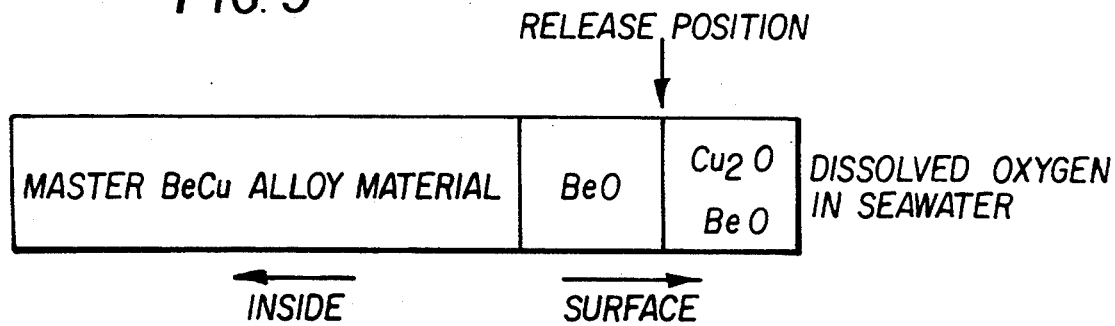
FIG. 4 is a schematic representation of a state of an oxide film of the beryllium-copper alloy according to the invention.

As well known from literature, the order of ionization tendency among beryllium, copper and nickel is expressed by Be>Ni>Cu In other words, beryllium ions are more likely to be liberated than copper ions, and copper ions are more likely to be liberated than nickel ions. In the case of a beryllium-copper combination, beryllium is first ionized to form a local cell, which has an effect on preventing deposition of oceanic life contaminants due to its current effect, while beryllium ions take on the form of internal oxidation. By this internal oxidation, a BeO film is first formed, as typically shown in FIG. 4. This BeO film, because of being porous, allows copper ions to be liberated, forming $Cu_2O + BeO$ on the surface. This liberation of copper ions into seawater produces an antifouling effect.

(2) Continued Action on Liberating Copper Ions

The above-mentioned effect (1) on preventing contamination makes another contribution to providing a continued liberation of copper ionst. That is, the beryllium-copper combination enables the antifouling function to be maintained ceaselessly. While in contact with seawater, the beryllium-copper combination forms on its surface an intimate surface oxide ($Cu_2O$), just below which a porous oxide film of BeO is formed, as can be seen from FIG. 4. Thus, the liberation of copper ions into seawater is maintained, while this film increases in volume by the oxidation. When the volume increase reaches a certain level, the surface oxide film peels away from the porous oxide or BeO layer. This would enable electrochemical action and the liberation of copper ions to be maintained over an extended period of time.

The continued action of the beryllium copper on the liberation of copper ions will now be explained with reference to FIG. 6 that is a graphic representation showing the results of comparison of beryllium copper with cupronickel.

Figure 6:
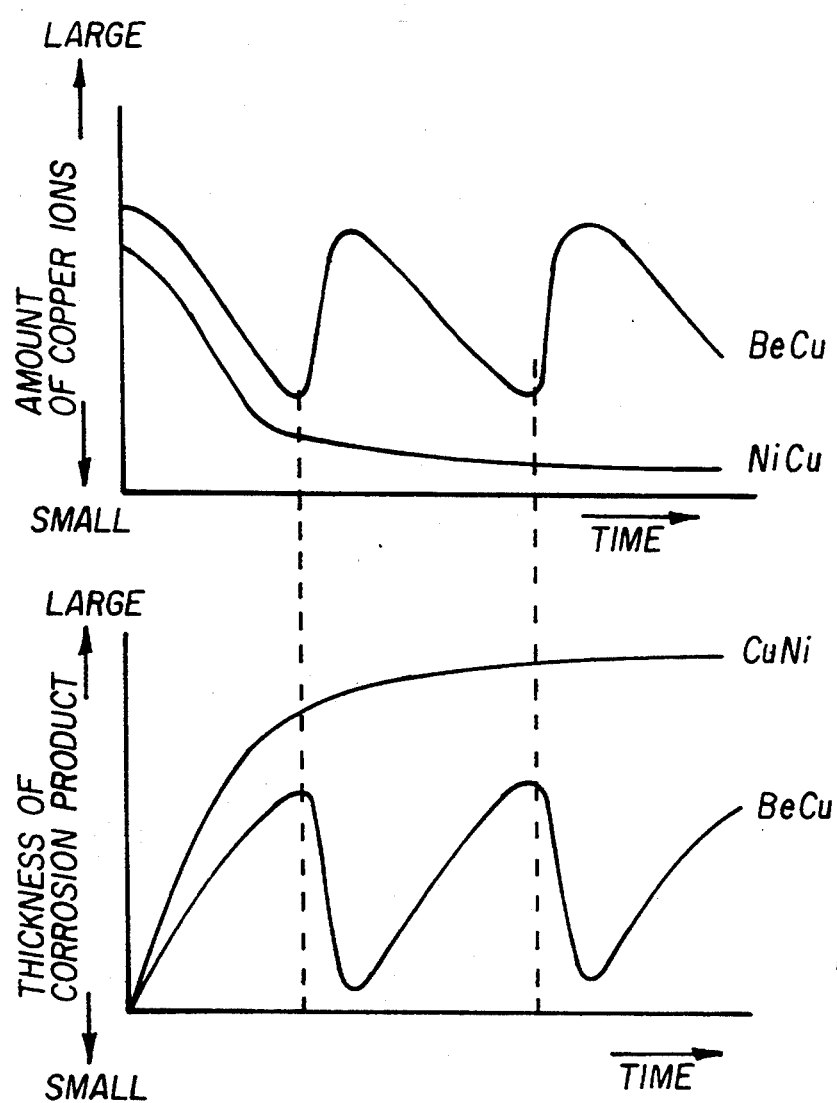
FIG. 6 is a schematic illustration wherein beryllium copper is compared with cupronickel in terms of changes over time of the amount of copper ions liberated and the thickness of corrosion product.

When the corrosion (oxidation) product reaches a certain thickness, it peels away from the beryllium copper (BeCu), as can be best seen from FIG. 6. Then, the beryllium-copper alloy is again exposed on the surface to seawater, and corroded or oxidized for oxide film growth. When this film grows to a certain thickness level, it peels away from the beryllium copper. This process is repeated over and over. The liberation of copper ions, on the other hand, is likely to be reduced with an increase in the thickness of the oxidation product. As the oxidation product peels away, however, the beryllium-copper alloy is again exposed on the surface to seawater, so that there can be an increase in the amount of the copper ions liberated. Thus, the increase and decrease in the amount of the copper ions liberated occur alternately.

The beryllium-copper alloy used in the invention enables copper ions to be continuously liberated by the peeling-off of the oxide film. As a result, the amount of contaminants deposited onto the surface of the beryllium copper is little, if any.

Figure 5:
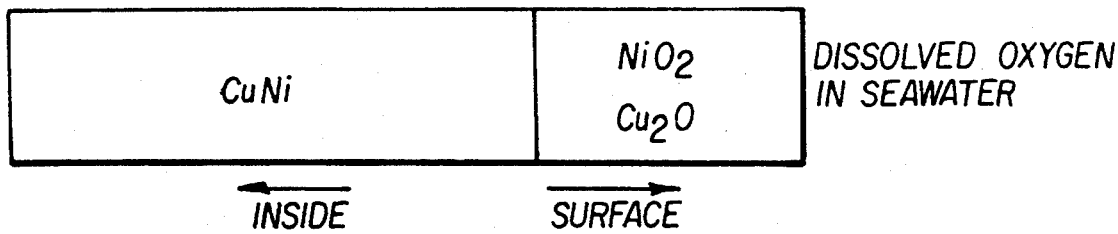
FIG. 5 is a schematic representation of a state an oxide film of a cupronickel, provided for comparative purposes.

This is in contrast to the comparative cupronickel (CuNi), as can be seen from FIG. 5. With the passing of some years, an intimate nickel oxide ($NiO_2$) or copper oxide ($Cu_2O$) layer is formed on the surface of the cupronickel, reducing the liberation of copper ions, as can be seen from FIG. 6. According to the order of ionization tendency (Be>Ni>Cu), this would be due to the fact the nickel (Ni) is preferentially ionized to form a local cell and so an intimate oxide is formed on the surface of the cupronickel, as can be seen from FIG. 5. As can be seen from FIG. 6, the thickness of the corrosion product on the cupronickel increases with time in an early stage, but its growth rate decreases as time goes by. With this, there is a decrease in the amount of the copper ions liberated. In addition, the corrosion product is less likely to peel away from the cupronickel that from the beryllium copper. Thus, the quantity of the copper ions liberated remains low, making the antifouling effect slender.

It is to be noted that the facts that a beryllium-copper alloy has a remarkable antifouling effect and provides a continued liberation of copper ions have been discovered by us for the first time. Insofar as we are concerned, never until now have such facts been referred to or indicated in literature.

It has also been confirmed that not only does a beryllium alloy pose no toxicity problem at all, but its service life in seawater is as long as that of aluminum pitch copper or white brass.

For practical beryllium alloys, various alloys inclusive of JIS 11 ALLOY having a beryllium content of 0.2 to 0.6% by weight and JIS 25 ALLOY having a beryllium content of 1.8 to 2.0% by weight are now available in the art. In view of the antifouling effect, however a beryllium content of at least 1.60% by weight is preferable. At a beryllium content higher than 2.8% by weight, beryllium does no longer form any further solid solution with copper. In other words, the resulting alloy excels in the antifouling effect but undergoes a gradual decrease in metalleability.

EMBODIMENTS OF THE FIRST ASPECT OF THE INVENTION

Referring now to FIG. 1, there is shown the first embodiment of the first aspect of the invention.

In the first embodiment, an insulating material layer 2 is formed on the surface of a thin sheet form of copper alloy layer 1 made up of, for instance, beryllium-copper alloy. This sheet form of antifouling structure 3 is in a thin sheet form, and is flexible as well. Preferably, the beryllium-copper alloy layer 1, for instance, may be formed of Be-Co, Be-Ni and Be-Co-Si base copper alloys.

For the insulating material layer 2, for instance, methyl methacrylate-modified natural rubber, nitrile rubber and chlorinated rubber may be used alone or in combination of two or more. The rubber is dissolved in a suitable solvent for priming or other treatments, coated on the required surface area of the beryllium alloy layer 1, and dried to obtain an insulating material layer having a given thickness. For instance, the insulating material layer 2 may have a thickness of about 5 to 20 mm, typically about 10 mm.

Figure 2:
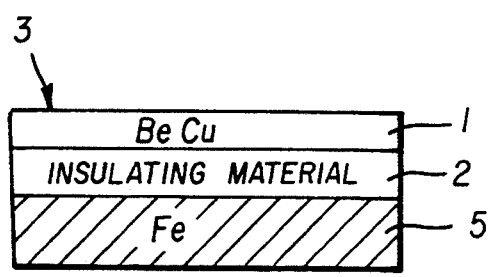
FIG. 2 is a schematic, sectional view showing the first embodiment of the antifouling structure that is bonded to the inner wall of a water intake pipe.

Practically, this antifouling structure 3 may be bonded to the inner face of a water intake pipe (water-circulation pipe), for instance. A typical example of the structure of the antifouling structure 3 is shown in FIG. 2. The water intake pipe 5 is formed of iron, and provided on the surface with the insulating material layer 2, which is then provided on the surface with the beryllium-copper alloy layer 1. It is this beryllium-copper alloy layer 1 that is exposed to seawater or water. It is here noted that the insulating material layer 2 is inhibited from corrosion due to a cell action, because the beryllium-copper alloy layer 1 is not in contact with the iron 5.

Figure 3:
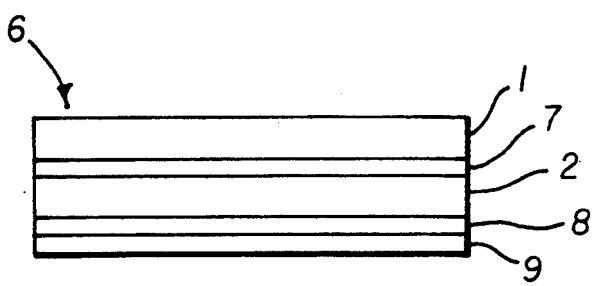
FIG. 3 is a schematic, sectional view of the second embodiment of the antifouling structure according to the first aspect of the invention.

The second embodiment of the first aspect of the invention is illustrated in FIG. 3.

This embodies an antifouling structure 6 that can be bonded to a metal member in contact with seawater, for instance, a water intake pipe.

The antifouling structure 6 comprises, in order from the surface, a beryllium-copper alloy layer 1, a primer layer 7, an insulating material layer 2, an adhesive material layer 8 and a release paper 9.

The primer layer 7 is interposed between the beryllium-copper alloy layer 1 and the insulating material layer 2, and is made of material that is well compatible with them for their bonding.

The adhesive material 8 is provided in the form of a layer of 0.05 to 2 mm in thickness.

The release paper 9 applied on the surface of the adhesive layer 8, is removed when the antifouling structure 6 is bonded to an application member. This release paper 9 is used to prevent one antifouling structure from sticking to another or something during storage or handling.

EMBODIMENTS OF THE SECOND ASPECT OF THE INVENTION

Figure 7:
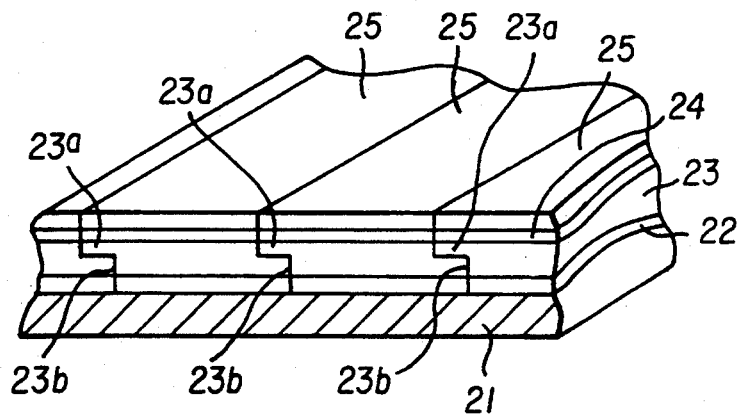
FIG. 7 is a partly cut-away, perspective view showing the first embodiment of the second aspect of the invention.
Figure 8:
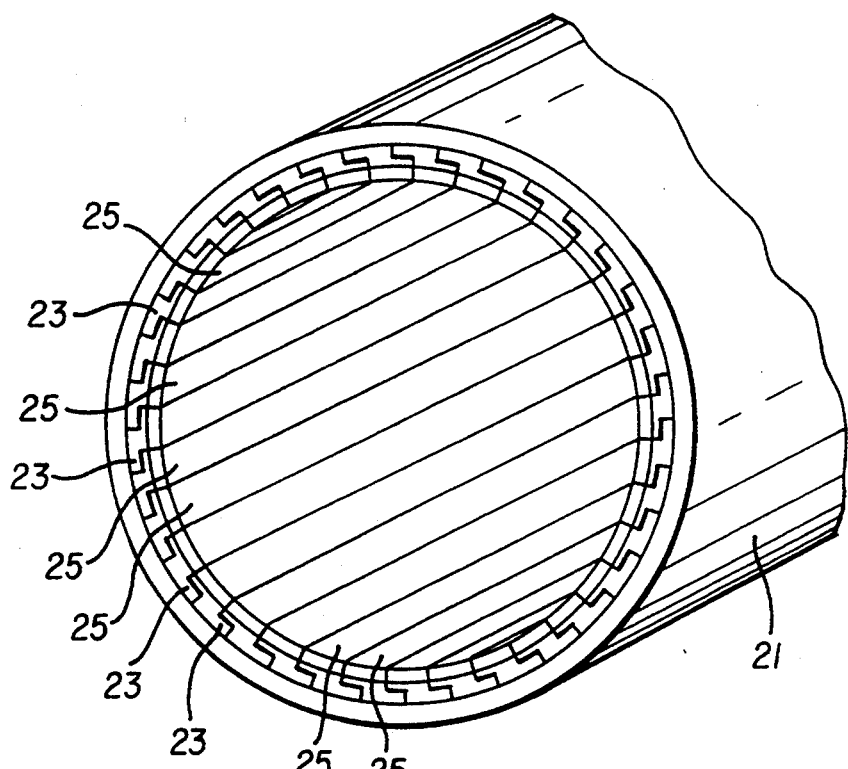
FIG. 8 is a perspective view showing an iron pipe used in the first embodiment of the second aspect of the invention.

The first embodiment of the second aspect of the invention will now be explained with reference to FIGS. 7 and 8.

This embodies the application of the invention to an iron pipe through which seawater flows.

An adhesive agent layer 22 is applied on the inner peripheral wall of a cylindrical iron pipe 21. A panel 23 formed of hard resin is fixed to the iron pipe 21 as by bolts, screws, etc., through the adhesive layer 22. An array of panels 23 are fixed in place by connecting the adjacent panels by male (23a)—and—female (23b) fitting. The adhesive agent layer 24 is coated on the surface of each panel 23, and a thin sheet form of beryllium-copper alloy 25 is applied to the adhesive agent layer 24.

This beryllium-copper alloy has a combined effect both on the exertion of the antifouling function and on the continued liberation of copper ions, as already mentioned.

Figure 9:
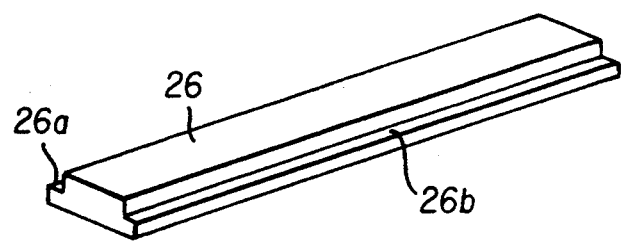
FIG. 9 is a representation of the shape of panels used in the second embodiment according to the second aspect of the invention.
Figure 10:
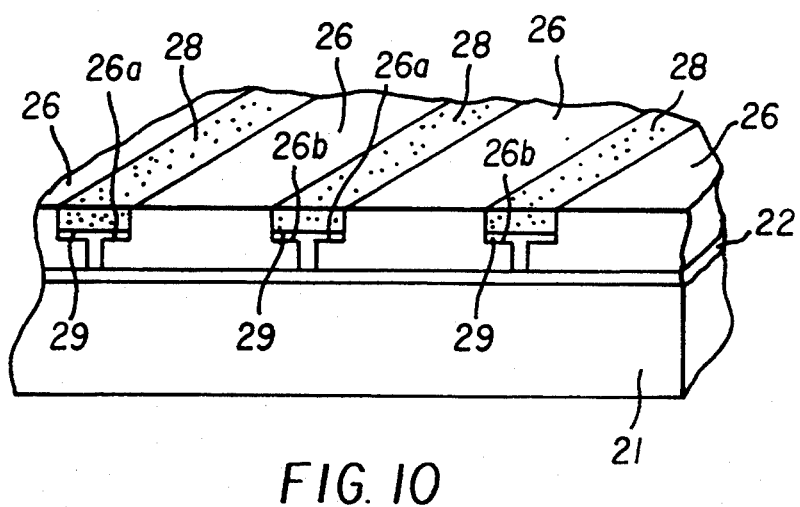
FIG. 10 is a partial perspective view showing an iron pipe used in the second embodiment according the second aspect of the invention.

The second embodiment of the second aspect of the invention will now be explained with reference to FIGS. 9 and 10.

This embodies the application (or lining) of a beryllium-copper alloy thin sheet to a part of the inner peripheral wall of the iron pipe 21 according to the first embodiment of the second aspect of the invention. An adhesive agent layer 22 is applied on the surface of the iron pipe 21, and an array of panels 26, each made of hard resin, is fixed on the adhesive layer 22 as by bolts, although not shown. These panels 26, each extending in the axial direction of the iron pipe 21, are juxtaposed with each other in the peripheral direction of the iron pipe 21. The beryllium-copper alloy thin sheet 28 is bonded by an adhesive agent 29 into recesses 26a and 26b formed in both edges of each panel 26.

Figure 11:
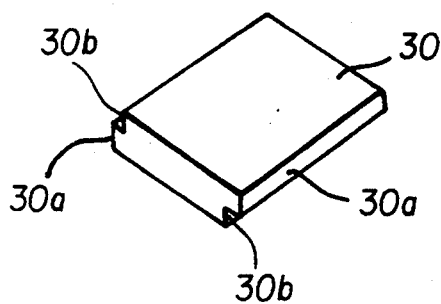
FIG. 11 is a perspective view showing panels used in the third embodiment according to the second aspect of the invention.
Figure 12:
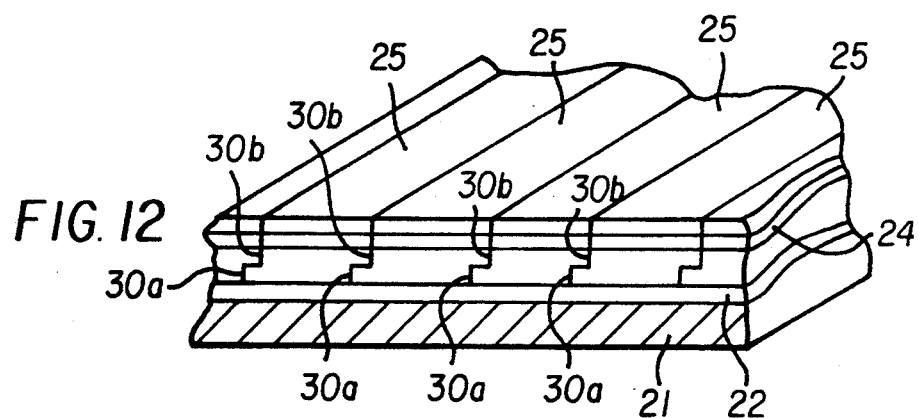
FIG. 12 is a sectional view showing an iron pipe used in the third embodiment according to the second aspect of the invention.

The third embodiment of the second aspect of the invention will now be explained with reference to FIGS. 11 and 12.

In this embodiment, a rectangular panel 30 is used instead of the panel 23 of continuous length according to the first embodiment. This rectangular panel 30, again formed of hard resin, may be applied to local areas of an iron pipe 21, for instance, its bends, corners, ends, and so on. This panel 30, because of being of small size, is favorably used to enhance the effect on the partial or local prevention of deposition of life contaminants. One rectangular panel 30 can be closely juxtaposed to the adjacent panels by male (30a)—and—female (30b) fitting. These panels are all of electrical insulating properties. As shown in FIG. 12, an adhesive agent layer 24 is applied on the surface of each panel 30, and a beryllium-copper alloy thin sheet is applied on the layer 24.

Figure 13:
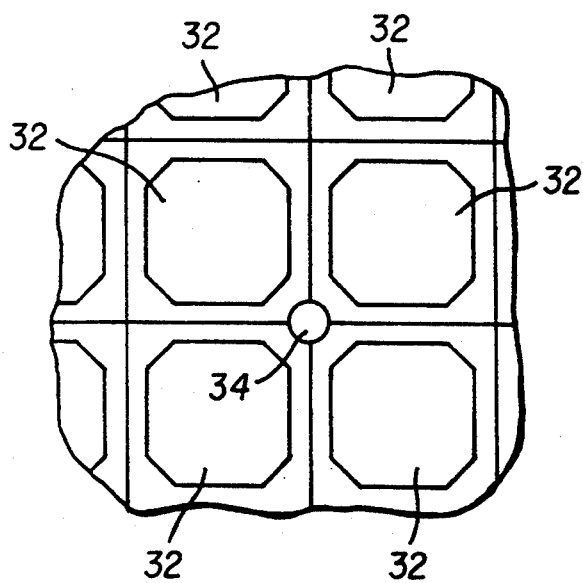
FIG. 13 is a plan view showing tiles used in the fourth embodiment according to the second aspect of the invention.
Figure 14:
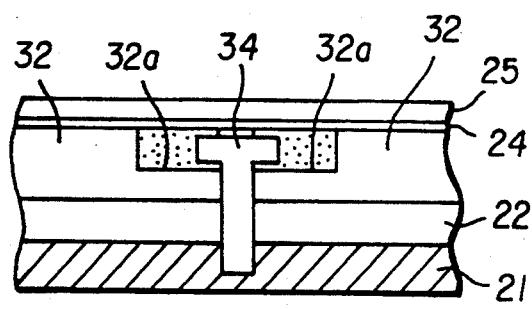
FIG. 14 is a sectional view showing an iron pipe used in the fourth embodiment according to the second aspect of the invention.

The fourth embodiment of the second aspect of the invention will be explained with reference to FIGS. 13 and 14.

In this embodiment, a beryllium-copper alloy is adhesively fixed onto a lattice array of rectangular, electrically insulating, ceramic tiles 32. Each tile 32 is provided with recesses 32a in and along its four sides. As illustrated, four tiles 32 are bolted at 34 such that they are firmly fixed to the iron pipe 21. Although not illustrated, a beryllium-copper alloy thin sheet 25 is applied on the surfaces of the tiles 32 through an adhesive agent layer 24.

EMBODIMENTS OF THE THIRD ASPECT OF THE INVENTION

Figure 15:
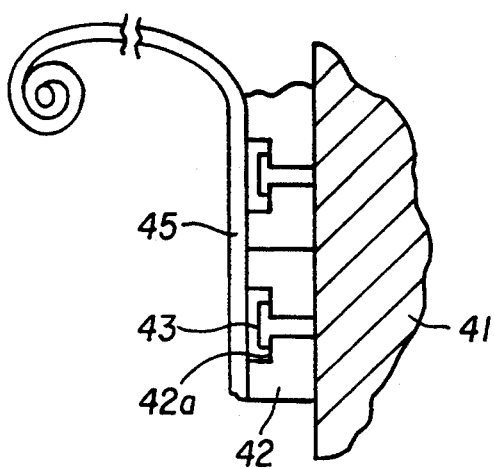
FIG. 15 is an illustration of how the antifouling structure is installed in the first embodiment according to the third aspect of the invention.

Illustrated in FIG. 15 is the first embodiment of the third aspect of the invention.

This embodies the application of the invention to a pipe for seawater circulation that is used in a power plant cooling system.

A tile 42 made of electrical insulating material is bolted at 43 on the inner peripheral wall of a cylindrical iron pipe 41. The tile 42 is in a polygonal sheet form. The head of the bolt 43 is located in a recess 42a formed in the tile 42. It is here noted that the depth of the recess 42a is larger than the height of the head of the bolt 43. One tile is closely juxtaposed to the adjacent tiles 42 on the iron pipe 41.

Then, a thin sheet 45 of beryllium copper 45 is applied onto the surface of each tile 42. This thin sheet 45 is provided in a rolled form, and is previously coated thereon with an adhesive agent.

Our years of experimentation and research teach us that a beryllium-copper alloy has a combined effect both on the exertion of the antifouling function and on the continued liberation of copper ions, as already mentioned.

Figure 16:
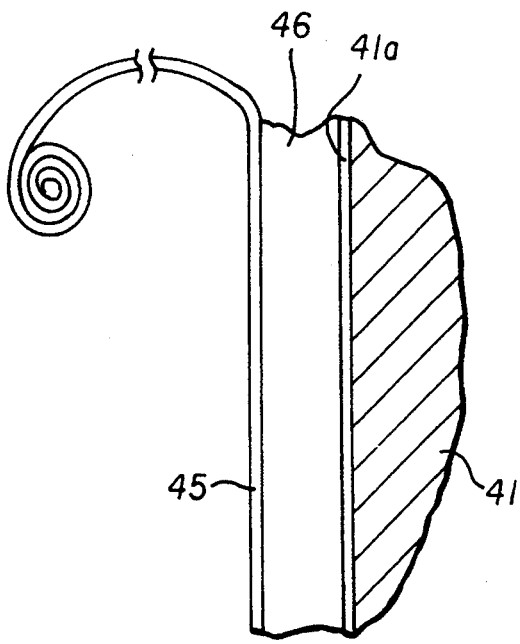
FIG. 16 is an illustration of how the antifouling structure is installed in the second embodiment according to the third aspect of the invention.

Illustrated in FIG. 16 is the second embodiment of the third aspect of the invention.

In this embodiment, an insulating material layer 46 is used in place of the tile 42 that is employed as the insulating material in the first embodiment.

The insulating material layer 46 is applied on the inner wall 41a of a pipe 41, and then dried, after which a thin sheet 45 made of a beryllium-copper alloy is applied on the layer 46. It is preferable to this end to use an adhesive agent or a beryllium-copper alloy thin sheet that has an adhesive agent applied on its surface.

The second embodiment is well resistant to a seawater attack, as in the case of the first embodiment, and so has a good-enough antifouling effect.

EMBODIMENTS OF THE FOURTH ASPECT OF THE INVENTION

Figure 17:
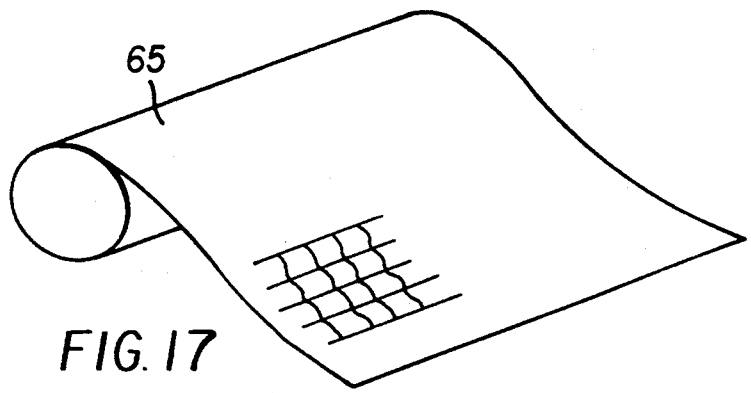
FIG. 17 is a perspective view showing a metal gauze of the first embodiment of the organism deposition-inhibiting structure according to the fourth aspect of the invention.

The first embodiment of the fourth aspect of the invention will now be explained with reference to FIGS. 17 and 18.

This embodies the application of the invention to a pipe for seawater circulation that is used in a power plant cooling system.

Figure 18:
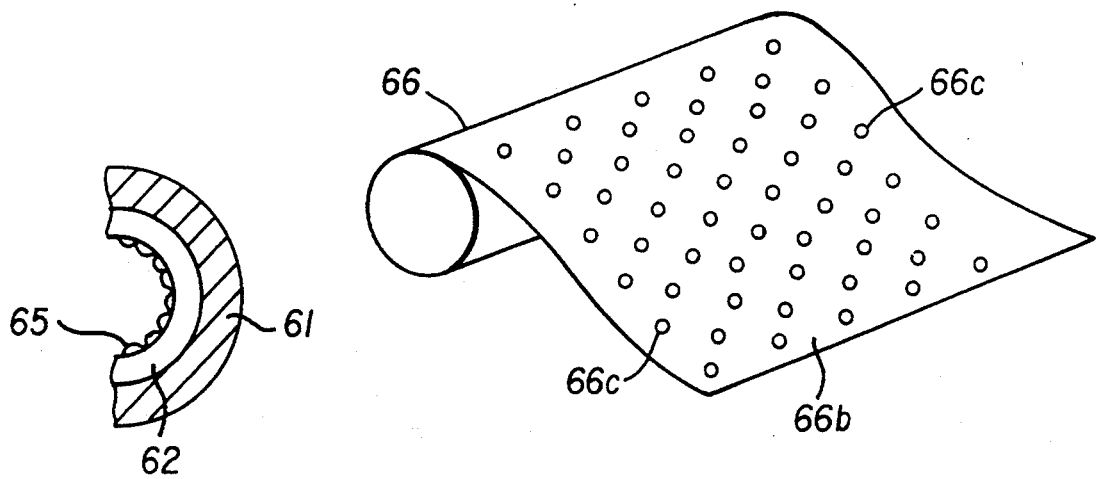
FIG. 18 is a schematic, sectional view showing the organism deposition-inhibiting structure to which the metal gauze shown in FIG. 17 is bonded.

As shown in FIG. 18, an electrical insulating glass, concrete or, preferably, resinous material 62 is bonded to the inner peripheral wall of a cylindrical iron pipe 61. Then, a metal gauze 65 made of beryllium copper is applied onto the surface of the resin 62. As shown in FIG. 17, the beryllium copper gauze 65 is provided in a rolled form, and the resin 62 has an adhesive layer on its surface.

Figure 19:
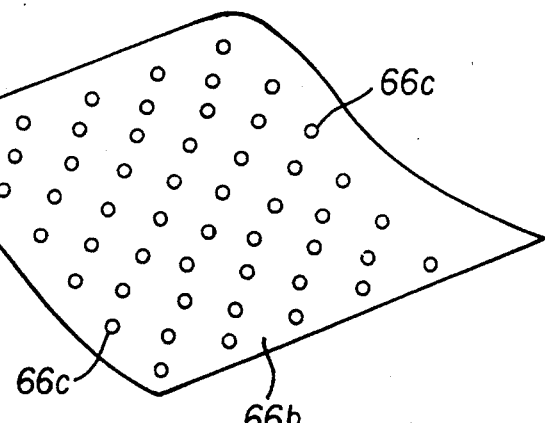
FIG. 19 is a perspective view showing a punching metal of the organism deposition-inhibiting structure according to the second embodiment according to the fourth aspect of the invention.

Illustrated in FIG. 19 is the second embodiment of the fourth aspect of the invention.

In this embodiment, a punching metal 66 is used for the metal gauze 65 in the first embodiment. The punching metal 66 is made of a beryllium-copper alloy, and comprises a foil member 66b having a number small holes 66c.

According to this embodiment, an insulating material layer 66 is coated on the inner peripheral wall 61a of a pipe 61, and then dried, after which the punching metal 66 is applied on the insulating material layer 66. It is preferable to this end to use an adhesive agent or a punching metal having an adhesive agent coated on its surface.

The second embodiment is well resistant to a seawater attack, as in the case of the first embodiment mentioned above, and so has an excellent antifouling effect.

Figure 20A:
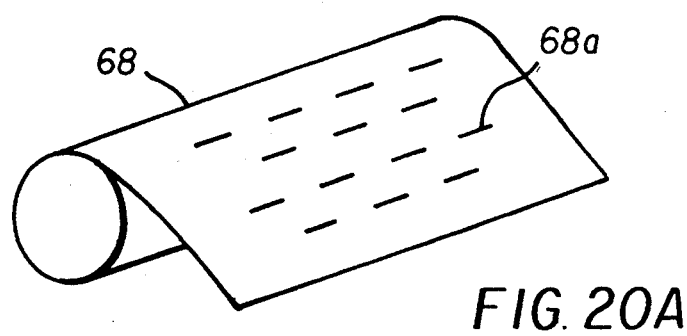
FIG. 20(A) is a perspective view showing a foil member of the organism deposition-inhibiting structure according to the third aspect of the invention.
Figure 20B:
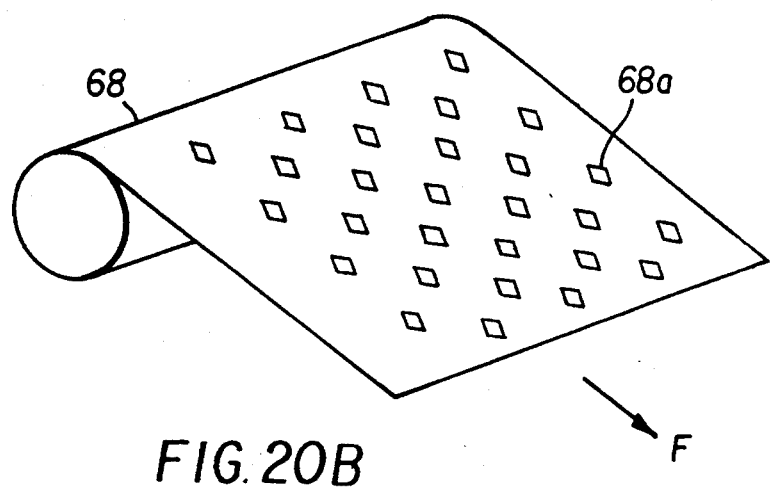
FIG. 20(B) is a perspective view showing the foil member to which tension is being applied.

Illustrated in FIG. 20 is the third embodiment of the fourth aspect of the invention.

In this embodiment, a foil member that is holed under tension is used in place of the punching metal 66 in the second embodiment. As shown in FIG. 20(A), the foil member 68 is made of a beryllium-copper alloy, and is provided with a number of slits 68a that deform into rectangular or round small holes 68a under tension.

Figure 21:
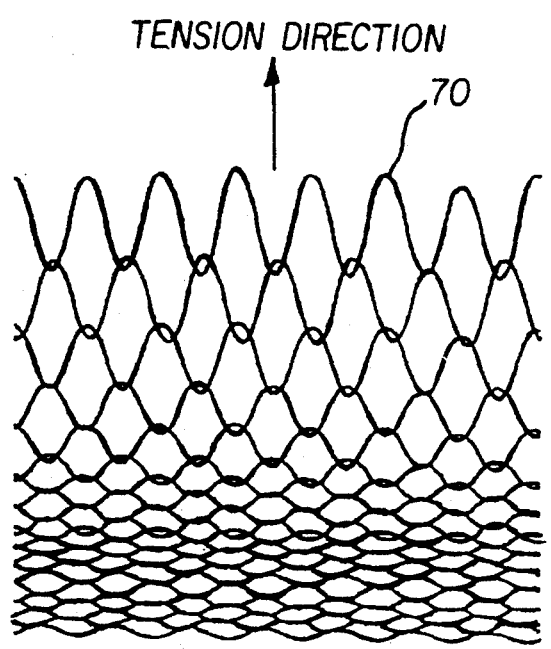
FIG. 21 is a perspective view showing a metal wire member of the organism deposition-inhibiting structure according to the fourth embodiment according to the fourth aspect of the invention.

Illustrated in FIG. 21 is the fourth embodiment of the fourth aspect of the invention.

In this embodiment, a metal wire member 70 that deforms into a metal gauze under tension is used in place of the punching metal 66 in the second embodiment. This metal wire member 70 is made of a beryllium-copper alloy, and deforms into a metal gauze upon tensioned in the direction shown by an arrow in FIG. 21.

With the antifouling structure constructed according to the first aspect of the invention, which has a copper alloy layer formed on its surface, a good-enough effect on the prevention of deposition of life contaminants is achieved partly because of the antifouling action of the copper alloy and partly because of the action of the copper alloy on the continued liberation of copper ions. In addition, this antifouling structure can be mounted in place with a good-enough working efficiency, because it is in a thin sheet form and possesses flexibility. Moreover, it assures that any corrosion due to a cell action can be avoided, because of the provision of the insulating material layer that inhibits the copper alloy from being in direct contact with the metal to be bonded.

The antifouling structure constructed according to the second aspect of the invention can be attached to iron sheets, iron pipes, etc., in simple operation, because it is not only of a unit type but of small size. In addition, it excels in corrosion resistance due to the provision of the insulator layer that inhibits electrolytic corrosion. Moreover, it can be maintained in less troublesome operation, offers no toxicity problem, and can effectively prevent deposition of oceanic organisms.

With the method for attaching an antifouling structure according to the third aspect of the invention, it is possible to attach the antifouling structure for inhibiting deposition of oceanic organisms in relatively simple operation. The antifouling structure provided by this method can be maintained in less troublesome operation, presents no toxicity problem, and can effectively inhibit deposition of marine organisms.

With the structure for inhibiting deposition of marine organisms according to the fourth aspect of the inventions, it is possible to install a structure for inhibiting marine deposits in relatively simple operation. The antifouling structure installed by this method excels in corrosion resistance, can be maintained in less troublesome operation, presents no toxicity problem, and can effectively inhibit marine deposits.

I claim:

1. An antifouling structure which is used on a surface of a marine structure exposed to seawater, to prevent deposition of marine organisms on said marine structure, comprising: a thin sheet including beryllium-copper alloy layer bonded to an insulating material layer, said beryllium-copper alloy layer having a beryllium content of at least 0.2% by weight.

2. The antifouling structure of claim 1, further comprising a metal member bonded to said insulating layer, opposite said beryllium-copper alloy layer.

3. The antifouling structure of claim 1, wherein said beryllium-copper alloy layer is bonded to said insulating material layer via an adhesive material layer.

4. The antifouling structure of claim 2, wherein said metal member is bonded to said insulating material layer via an adhesive layer.

5. A structure which is resistant to deposition of marine organisms when exposed to seawater, comprising:
a metal member having a surface;
an insulator layer provided on said surface of said metal member; and
a beryllium-copper alloy metal gauze which is bonded to said insulator layer, said beryllium-copper alloy metal gauge having a beryllium content of at least 0.2% by weight.

6. The structure of claim 5, wherein said beryllium-copper alloy comprises 0.2 to 2.8% by weight beryllium, and at least one material selected from the group consisting of Co, Si and Ni.

7. The structure of claim 6, wherein beryllium-copper alloy is an alloy selected from the group consisting of Be-Cu, Be-Co-Cu, Be-Co-Si-Cu and Be-Ni-Cu alloys.

8. The structure of claim 7, wherein said insulator layer comprises a resin.

9. A structure which is resistant to deposition of marine organisms when exposed to seawater, comprising:
a metal member having a surface;
an insulator layer formed on said surface of the metal member; and
a beryllium-copper foil member which is bonded to said insulator layer and having a beryllium content of at least 0.2% by weight.

10. A method for attaching an antifouling structure to a metal member, said antifouling structure being resistant to deposition of marine organisms when exposed to seawater, comprising the steps of:
forming an insulator layer on a surface of a metal member; and
bonding a thin sheet comprised of beryllium-copper alloy having a beryllium content of at least 0.2% by weight to a surface of the insulator layer.

11. The method of claim 10, wherein said beryllium-copper alloy comprises 0.2 to 2.8% by weight beryllium, and at least one material from the group consisting of Co, Si and Ni.

12. The method of claim 11, wherein said beryllium-copper alloy is an alloy selected from the group consisting of Be-Cu, Be-Co-Cu, Be-Co-Si-Cu and Be-Ni-Cu alloys.

13. The method of claim 12, wherein said insulator layer is comprised of a tile or panel.

* * * * *